(12) United States Patent
Sofranko et al.

(10) Patent No.: US 9,308,339 B2
(45) Date of Patent: Apr. 12, 2016

(54) PATIENT INTERFACE HAVING WRAP AROUND FABRIC HEADGEAR

(75) Inventors: Richard Andrew Sofranko, Eindhoven (NL); Joshua Mark Greenberg, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 173 days.

(21) Appl. No.: 13/994,309

(22) PCT Filed: Dec. 13, 2011

(86) PCT No.: PCT/IB2011/055633
§ 371 (c)(1),
(2), (4) Date: Jun. 14, 2013

(87) PCT Pub. No.: WO2012/085755
PCT Pub. Date: Jun. 28, 2012

(65) Prior Publication Data
US 2013/0263860 A1  Oct. 10, 2013

Related U.S. Application Data

(60) Provisional application No. 61/424,881, filed on Dec. 20, 2010.

(51) Int. Cl.
*A61M 11/00* (2006.01)
*A61M 16/00* (2006.01)
(Continued)

(52) U.S. Cl.
CPC ............ *A61M 16/0057* (2013.01); *A61M 16/06* (2013.01); *A61M 16/0666* (2013.01); *A61M 16/0683* (2013.01); *A61M 16/0875* (2013.01); *A61M 2210/0618* (2013.01)

(58) Field of Classification Search
CPC ............ A61M 16/0683; A61M 16/06; A61M 16/0816; A61M 16/0666; A61M 16/0622; A61M 16/0057; A61M 16/0875; A61M 2210/0618

USPC ............ 128/207.11, 206.24, 205.25, 206.21, 128/848

See application file for complete search history.

(56) References Cited

U.S. PATENT DOCUMENTS 4,848,334 A   7/1989  Bellm
5,735,270 A   4/1998  Bayer
(Continued)

FOREIGN PATENT DOCUMENTS

CN          1684733 A     10/2005
CN        101489617 A      7/2009
(Continued)

OTHER PUBLICATIONS

CPAP Chin Strap, Oct. 26, 2010 Source: http://www.tinashomecare.com/cpap_chin_straps.htm.
(Continued)

*Primary Examiner* — Steven Douglas
(74) *Attorney, Agent, or Firm* — Michael W. Haas

(57) ABSTRACT

A patient interface device includes a headgear component having a first end, a second end, and a sealing interface region located between the first end and the second end, wherein the sealing interface region has a hole extending through the elongated fabric body member. The patient interface device also includes a mask component having a cushion and a fluid coupling conduit fluidly coupled to the cushion, wherein at least a portion of the fluid coupling conduit extends through the hole and the sealing interface region covers at least a portion of the cushion. The cushion will be held and supported by the elongated fabric body member in engagement with a portion of the patient's face responsive to the patient interface device being donned by the patient by wrapping the elongated fabric body member around the head of the patient.

18 Claims, 7 Drawing Sheets

(51) Int. Cl.
*A61M 16/06* (2006.01)
*A61M 16/08* (2006.01)

(56) References Cited

U.S. PATENT DOCUMENTS

| | | | |
|---|---|---|---|
| 5,803,077 A * | 9/1998 | Gazzara | 128/205.27 |
| 6,941,949 B2 * | 9/2005 | Amante et al. | 128/206.21 |
| 7,624,735 B2 * | 12/2009 | Ho et al. | 128/207.11 |
| 7,721,737 B2 | 5/2010 | Radney | |
| 8,851,078 B2 * | 10/2014 | Newman et al. | 128/848 |
| 2004/0078869 A1 | 4/2004 | Bell | |
| 2004/0083534 A1 * | 5/2004 | Ruiz et al. | 2/171.2 |
| 2007/0101996 A1 | 5/2007 | Carstens | |
| 2008/0060654 A1 * | 3/2008 | Vandine | 128/207.11 |
| 2010/0018534 A1 | 1/2010 | Veliss | |

FOREIGN PATENT DOCUMENTS

| | | |
|---|---|---|
| CN | 101653632 A | 2/2010 |
| CN | 101678085 A | 3/2010 |
| WO | WO2008030831 A2 | 3/2008 |
| WO | WO2009109005 A1 | 9/2009 |
| WO | WO2010139014 A1 | 12/2010 |

OTHER PUBLICATIONS

BreathXchange Fleece Mask, Oct. 26, 2010 Source: http://www.kaboodle.com/reviews/breathxchange-fleece-mask-18179.

* cited by examiner

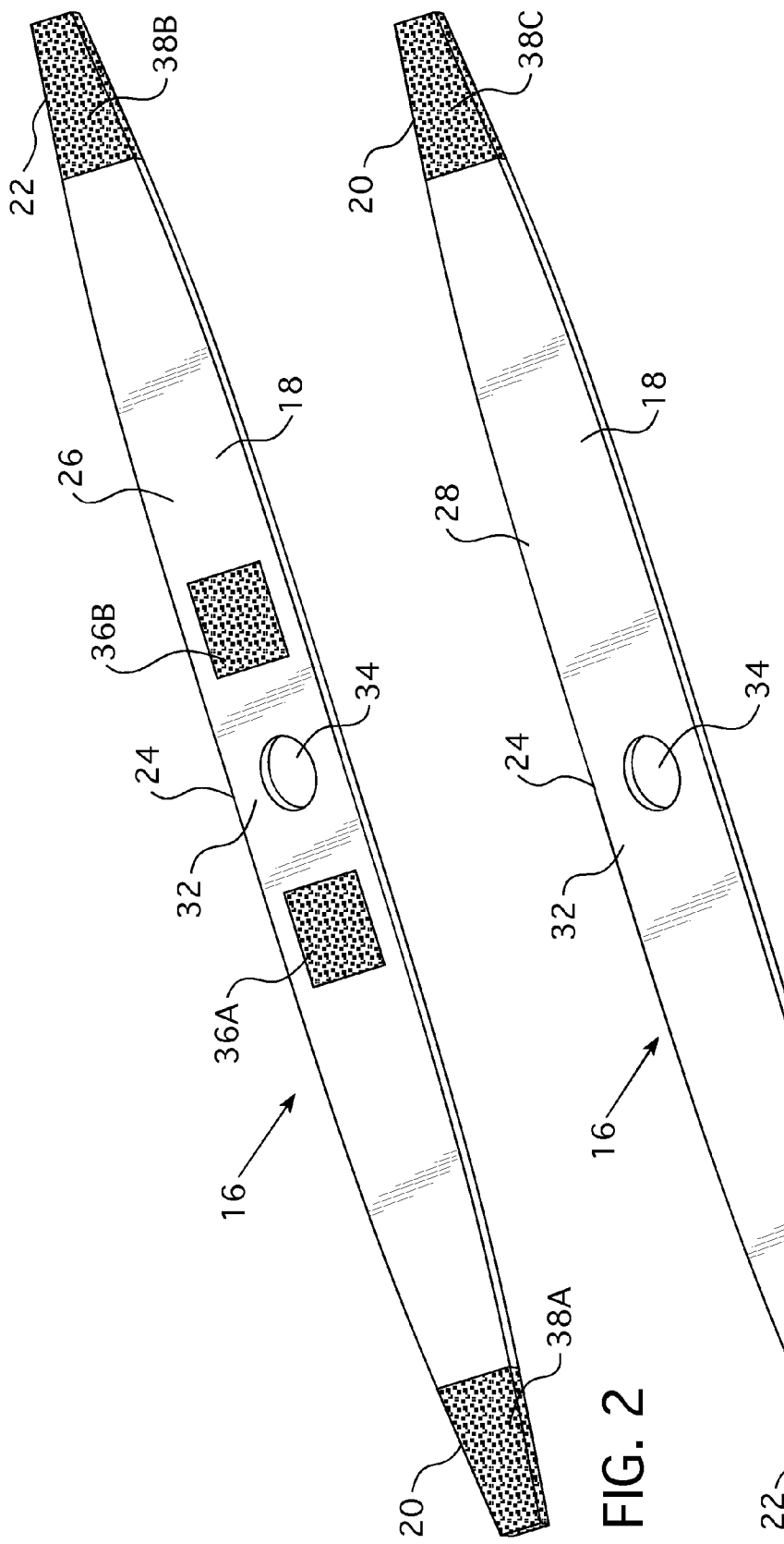

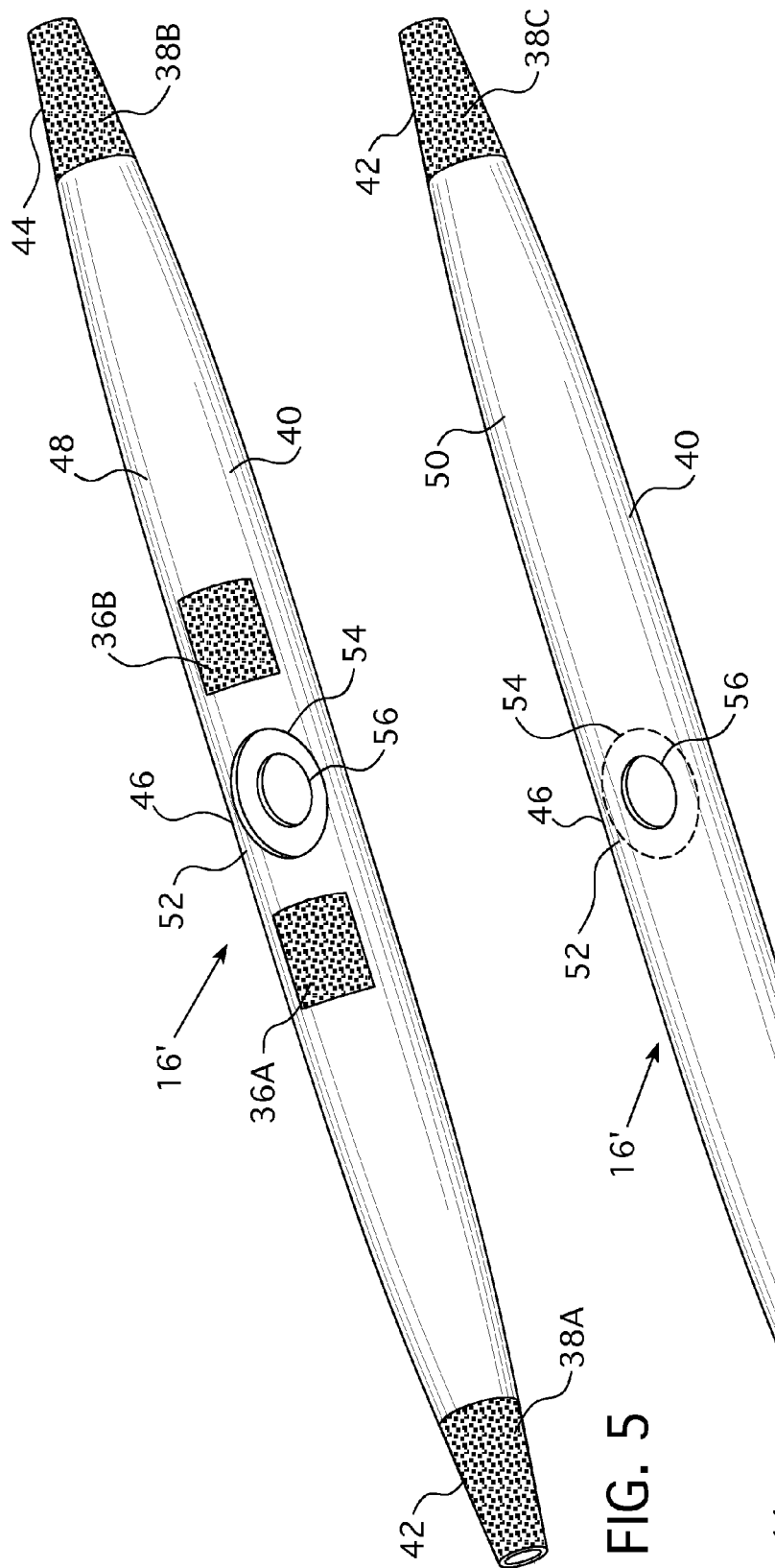

PATENT INTERFACE HAVING WRAP AROUND FABRIC HEADGEAR

CROSS-REFERENCE TO RELATED APPLICATIONS

This patent application claims the priority benefit under 35 U.S.C. §371 of international patent application no. PCT/IB2011/055633, filed Dec. 13, 2011, which claims the priority benefit under 35 U.S.C. §119(e) of U.S. Provisional Application No. 61/424,881 filed on Dec. 20, 2010, the contents of which are herein incorporated by reference.

BACKGROUND OF THE INVENTION

1. Field of the Invention

The present invention relates to respiratory patient interface devices, and, in particular, to a patient interface device having a fabric headgear structured to wrap around the patient's head.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Adherence and compliance to therapy, such as CPAP or other pressure support therapies, is growing to be an industry-wide issue. Factors such as comfort and ease of a patient interface device can greatly affect a patient's adherence and compliance to therapy. Thus, easier to use, simplified designs for patient interface devices are becoming expectations for any product that seeks to compete.

SUMMARY OF THE INVENTION

Accordingly, it is an object of the present invention to provide a patient interface device that overcomes the shortcomings of conventional patient interface devices. This object is achieved according to one embodiment of the present invention by providing a patient interface device that includes a headgear component including an elongated fabric body member structured to wrap around the head of a patient. The elongated fabric body member has a first end, a second end, and a sealing interface region located between the first end and the second end, wherein the sealing interface region has a hole extending through the elongated fabric body member. The patient interface device also includes a mask component having a cushion and a fluid coupling conduit fluidly coupled to the cushion, wherein at least a portion of the fluid coupling conduit extends through the hole and the sealing interface region covers at least a portion of the cushion. In this embodiment, the cushion will be held and supported by the elongated fabric body member in engagement with a portion of the patient's face responsive to the patient interface device being donned by the patient by wrapping the elongated fabric body member around the head of the patient.

In another embodiment, a method of securing a patient interface device to the head of a patient is provided, wherein the patient interface device includes a mask component having a cushion and a fluid coupling conduit fluidly coupled to the cushion. The method includes obtaining a headgear component including an elongated fabric body member structured to wrap around the head of the patient, the elongated fabric body member having a first end, a second end and a sealing interface region located between the first end and the second end, the sealing interface region having a hole extending through the elongated fabric body member. The method further includes inserting a portion of the fluid coupling conduit through the hole such that the sealing interface region covers at least a portion of the cushion, positioning the cushion against a portion of the patient's face, and wrapping the elongated fabric body member around the head in a manner wherein the cushion will be held and supported by the elongated fabric body member in engagement with the portion of the patient's face.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 2 is a rear perspective view and FIG. 3 is a front perspective view of a headgear component according to one exemplary embodiment of the present invention forming a part of the system of FIG. 1;

FIG. 5 is a rear perspective view and FIG. 6 is a front perspective view of a headgear component according to another exemplary embodiment of the present invention forming a part of the system of FIG. 4;

DETAILED DESCRIPTION OF EXEMPLARY EMBODIMENTS

Figure 1:
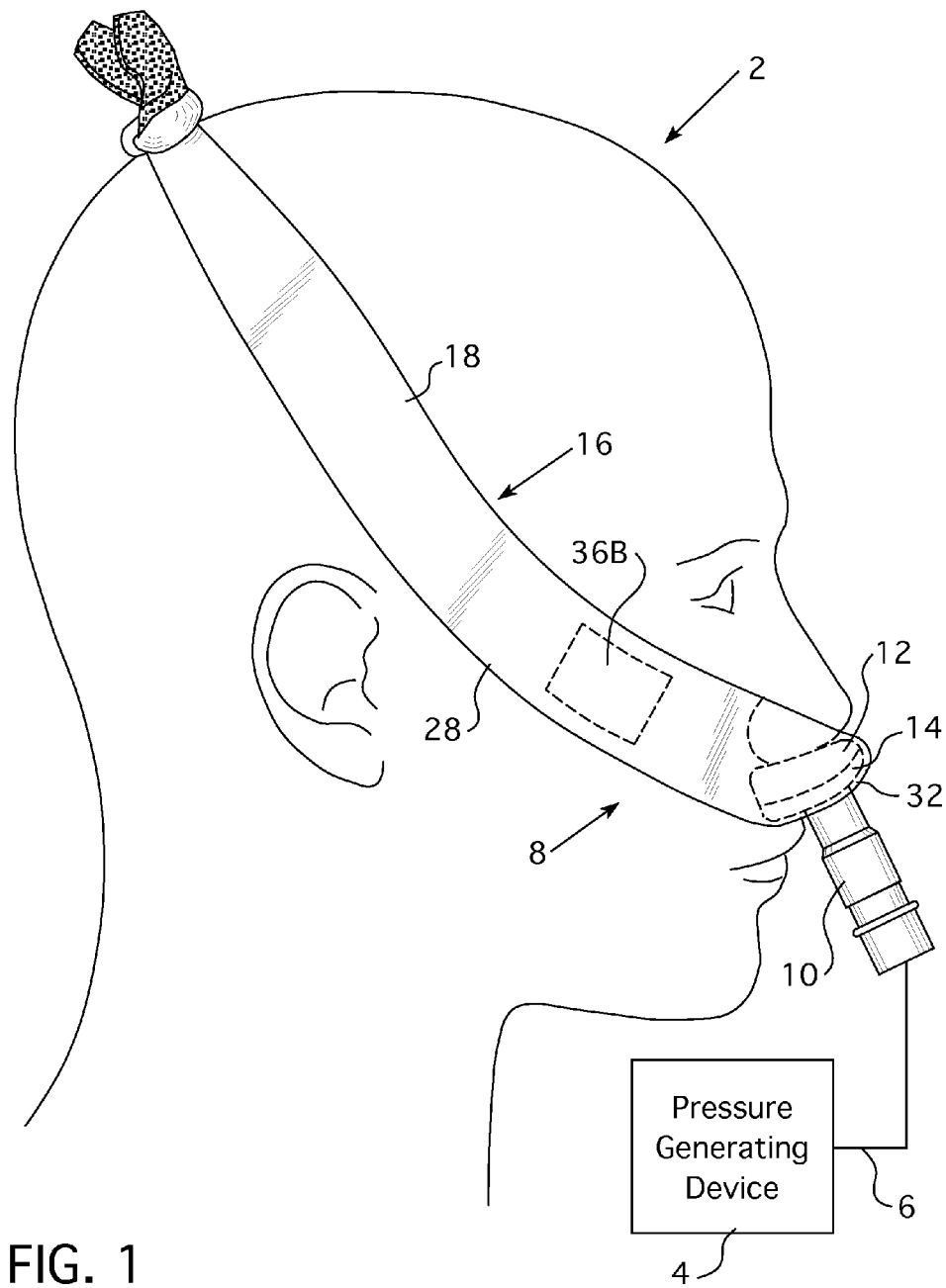
FIG. 1 is a schematic diagram of a system adapted to provide a regimen of respiratory therapy to a patient according to one exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment is generally shown in FIG. 1. System 2 includes a pressure generating device 4, a patient circuit 6, and a patient interface device 8 having a fluid coupling conduit 10 (e.g., an elbow conduit). Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Patient circuit 6 is structured to communicate the flow of breathing gas from pressure generating device 4 to patient interface device 8, and typically includes a gas delivery conduit or tube coupled to fluid coupling conduit 10.

In the illustrated embodiment, patient interface 8 is a nasal saddle type cushion structured to be placed against the lower, underside portion of the nose of a patient (wherein the patient's nares are engaged and covered). Any type of patient interface device 8, however, such as a nasal cushion having nasal prongs that are received within the patient's nares, a nasal mask that covers the nose, a nasal/oral mask that covers the nose and mouth, or a full face mask that covers the patient's face, which facilitates the delivery of the flow of breathing gas to, and the removal of a flow of exhalation gas from, the airway of such a patient may be used while remaining within the scope of the present invention.

In the embodiment shown in FIG. 1, patient interface 8 includes a cushion 12, which is coupled to a rigid or semi-rigid frame or faceplate 14. An opening in frame 14 to which fluid coupling conduit 10 is coupled allows the flow of breathing gas from pressure generating device 4 to be communicated to an interior space defined by cushion 12, and then, to the airway of a patient. The opening in frame 14 also allows the flow of exhalation gas (from the airway of such a patient) to be communicated to an exhaust port that may be provided, for example and without limitation, in fluid coupling conduit 10 or elsewhere on the patient interface device 8. Patient interface 8 further includes a headgear component 16 configured to secure patient interface device 8 to the patient's head. As described in greater detail below, in the exemplary embodiment, headgear component 16 comprises a single piece wrap-around fabric member structured to be wrapped around the head of the patient such that cushion 12 is held in place within/beneath it and against the face of the patient in a manner that permits gases to be communicated to and from the airway of the patient through cushion 12.

FIG. 2 is a rear elevational view and FIG. 3 is a front elevational view of headgear component 16 according to one exemplary embodiment of the present invention. Headgear component 16 includes a flat, elongated body 18 made of a fabric material. As used herein, the term "fabric" shall mean a material consisting of a network of natural or artificial fibers made by, for example and without limitation, interlacing weaving, knitting, spreading, crocheting, or bonding the fibers to form the network. Body member 18 may be made from any of a number of suitable fabric materials, such as, without limitation, Lycra® (or another type of spandex material), silk, or polyester. Body member 18 includes a first end 20, a second end 22 opposite first end 20, a central region 24 located about midway between first end 20 and second end 22, a rear surface 26 (FIG. 2) and a front surface 28 (FIG. 3).

Central region 24 includes a sealing interface region 32 having a hole 34 extending through body member 18. As seen in FIG. 1, and as described elsewhere herein, hole 34 is structured to receive fluid coupling conduit 10 therethough when patient interface device 8 is donned by the patient. Central region 24 also includes first and second stabilizing regions 36A, 36B provided on rear surface 26 adjacent to and on opposite sides of sealing interface region 32. In the exemplary embodiment, each stabilizing region 36A, 36B comprises an elastomeric webbing made by coating the fibers of the fabric material of body member 18 in that region with an elastomer coating. For example, the fibers of the fabric material of body member 18 in that region may be overmolded with an elastomer material, such as, without limitation, liquid silicone rubber, polyurethane, or gel, to produce first and second stabilizing regions 36A, 36B.

In first and second stabilizing regions 36A, 36B, the elastomer coating is primarily on the fibers only, allowing interstices through the fabric such that, when stretched, the fabric can allow the passage of air. The first and second stabilizing regions 36A, 36B thus provide a stabilizing, slide prevention area on either side of sealing interface region 32 such that torque due to, for example, pulling on a hose forming part of patient circuit 6 during use is absorbed within the elastomeric webbing and fleshy regions of the patient's face that are in contact with the elastomeric webbing.

As just described, in the illustrated embodiment, first and second stabilizing regions 36A, 36B are made by coating the fibers of body member 18 themselves. Alternatively, each stabilizing regions 36A, 36B may be a separate webbing component attached to rear surface 26 such as by an adhesive or stitching wherein each separate webbing component comprises a fabric having fibers that are coated by an elastomer as described elsewhere herein.

As a further alternative, first and second stabilizing regions 36A, 36B may be made from elastomers with a rough texture or a gel-like substance that provides a sticky or high friction surface.

In addition, in the exemplary embodiment, first end 20 and second end 22 each include an elastomeric webbing portion 38 (labeled 38A, 38B, 38C and 38D in FIGS. 1 and 2) provided on rear surface 26 and front surface 28. As described elsewhere herein, each elastomeric webbing portion 38 may be made by coating certain of the fibers of body member 18 themselves, or, alternatively, each elastomeric webbing portion 38 may be a separate webbing component attached to rear surface 26 and front surface 28 such as by an adhesive or stitching. The function of elastomeric webbing portions 38 is described below.

When patient interface device 8 is to be used by a patient, the patient first attaches fluid coupling conduit 10 to frame 14 as described elsewhere herein and then inserts fluid coupling conduit 10 through hole 34 from rear surface 26 to front surface 28. When this is done, at least part of cushion 12 will be covered by the part of sealing interface region 32 surrounding hole 34. The patient then positions cushion 12 against his or her nose as directed and wraps body member 18 around his or her head as shown in FIG. 1. First end 20 and second end 22 can then be tied in a half or full knot to secure headgear component 16 in place. When the knot is tied as just described, elastomeric webbing portions 38 will facilitate a secure coupling due to the interstices contained therein and the tendency of the elastomer to adhere to itself. Alternatively, rather than tying a knot as just described, first end 20 and second end 22 can simply be pressed against each other and twisted. When this is done, elastomeric webbing portions 38 will bind to each other without the necessity of tying a knot due to the stretch of the fabric and the characteristics of the elastomeric webbing. In particular, due to the interstices contained in elastomeric webbing portions 38 and the tendency of the elastomer to adhere to itself, a binding of the first end 20 and second end 22 is accomplished across the area of the elastomeric webbing portions 38. As still another alternative, a connection system such as a hook and loop fastener system (e.g., Velcro®) or some other suitable fastener system may be employed to couple first end 20 and second end 22 together.

Furthermore, when headgear component 16 is donned as just described, first and second stabilizing regions 36A, 36B will engage the face of the patient, and in particular the cheeks of the patient. As described elsewhere herein, when this engagement occurs, first and second stabilizing regions 36A, 36B will provide a stabilizing, slide prevention function for patient interface device 8 to comfortably hold it in place.

Figure 4:
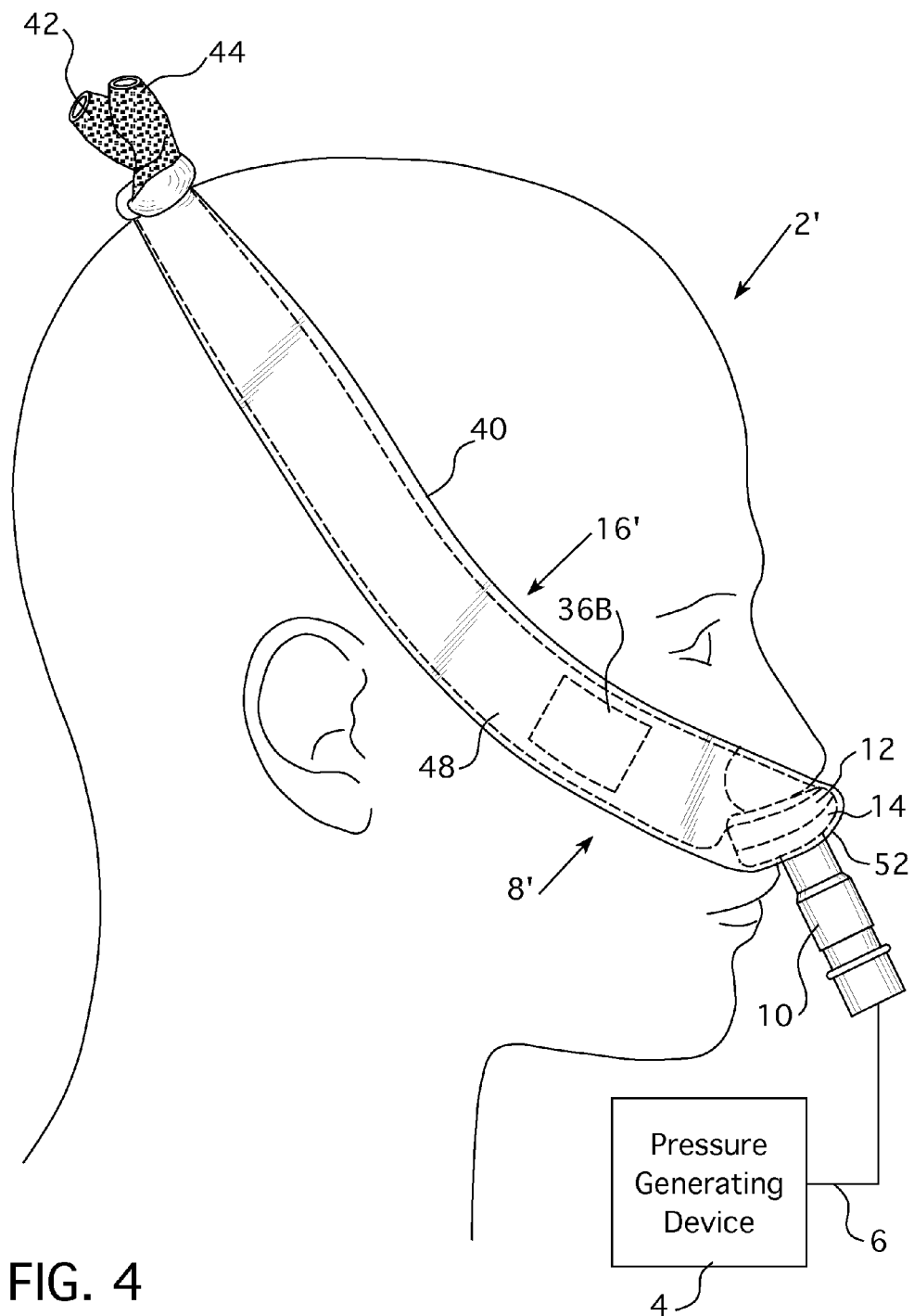
FIG. 4 is a schematic diagram of a system adapted to provide a regimen of respiratory therapy to a patient according to an alternative exemplary embodiment of the present invention.

A system 2' adapted to provide a regimen of respiratory therapy to a patient according to an alternative exemplary embodiment is generally shown in FIG. 4. System 2' includes a number of the same components as system 2 shown in FIG. 1, and like components are labeled with like reference numerals. System 2', however, includes a patient interface device 8' having a headgear component 16' according to an alternative exemplary embodiment of the present invention. FIG. 5 is a rear elevational view and FIG. 6 is a front elevational view of headgear component 16'. Headgear component 16', described in detail below, includes a number of the same components as headgear component 16 shown in FIGS. 2 and 3, and like components are labeled with like reference numerals.

Referring to FIGS. 5 and 6, headgear component 16' includes a hollow, tubular, elongated body member 40 made of a fabric material. Body member 40 may be made from any of a number of suitable fabric materials, such as, without limitation, Lycra® (or another type of spandex material), silk, or polyester. Body member 40 includes a first end 42, a second end 44 opposite first end 42, a central region 46 located about midway between first end 42 and second end 44, a rear surface 48 (FIG. 5) and a front surface 50 (FIG. 6).

Central region 46 includes a sealing interface region 52 having a first hole 54 extending through rear surface 48 and a second, smaller hole 56 extending through front surface 50. As seen in FIG. 4, a space/pocket formed between rear surface 48 and front surface 50 is structured to receive and hold a portion of cushion 12 and at least a portion of frame 14. More specifically, hole 56 is structured to receive fluid coupling conduit 10 therethough when patient interface device 8 is donned by the patient. When this is done, the sealing surface of cushion 12 will extend outwardly from hole 54 so that it will be in a position to engage the face (e.g., nose) of the patient.

Central region 46 also includes first and second stabilizing regions 36A, 36B formed as described elsewhere herein in various embodiments. As seen in FIG. 5, first and second stabilizing regions 36A, 36B are provided on rear surface 48 adjacent to and on opposite sides of sealing interface region 46. In addition, in the exemplary embodiment, first end 42 and second end 44 each include an elastomeric webbing portion 38 (labeled 38A, 38B, 38C and 38D in FIGS. 5 and 6) formed as described elsewhere herein on rear surface 48 and front surface 50.

Patient interface device 8' maybe donned for use by a patient in essentially the same manner as patient interface device 8. When this is done, the elastomeric webbing portions (36A, 36B, 38A, 38B, 38C, 38D) will perform provide the same functionality that was described elsewhere herein in connection with FIGS. 1-3.

Figure 7:
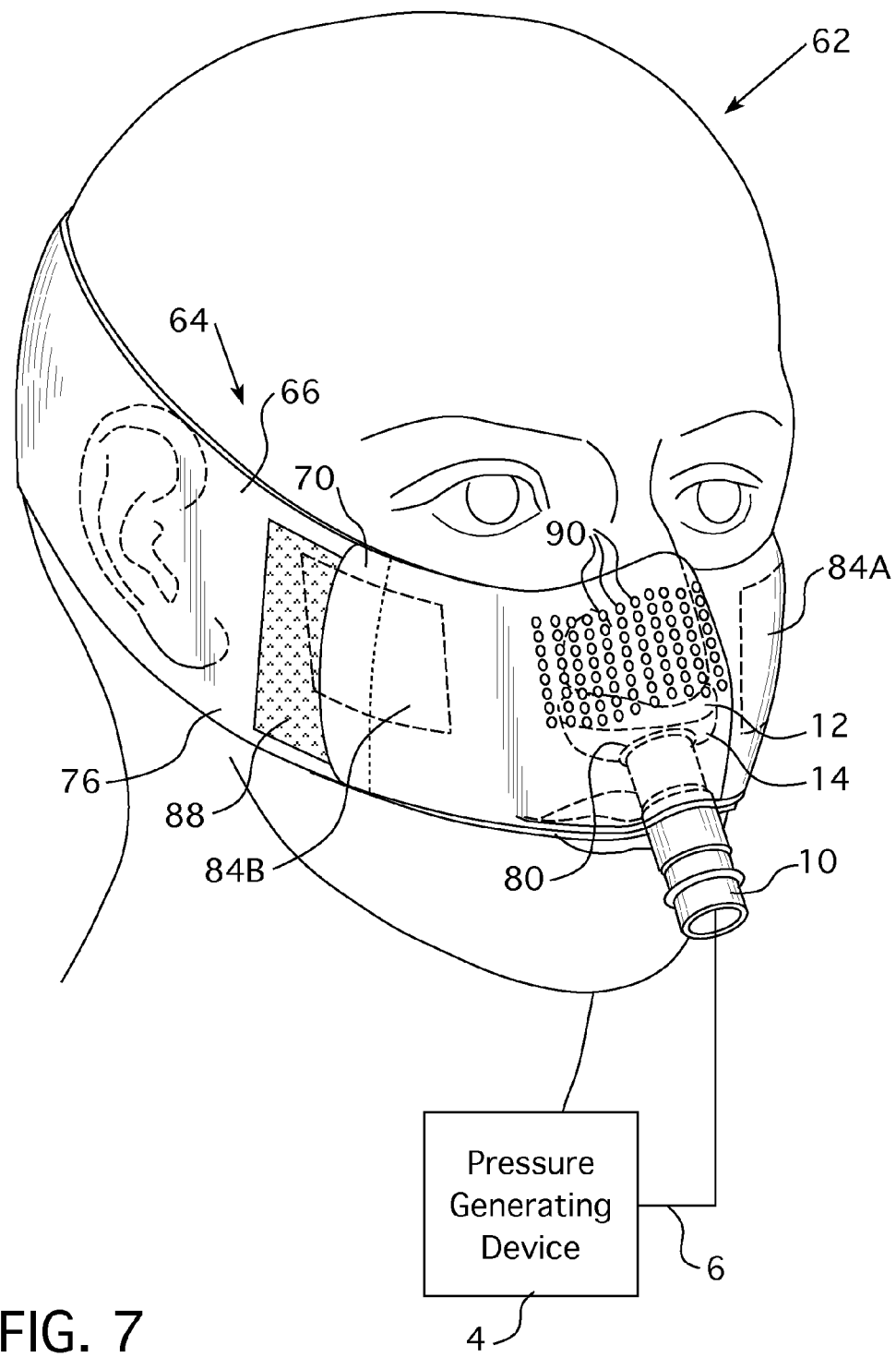
FIG. 7 is a schematic diagram of a system adapted to provide a regimen of respiratory therapy to a patient according to another alternative exemplary embodiment of the present invention.

A system 60 adapted to provide a regimen of respiratory therapy to a patient according to another alternative exemplary embodiment is generally shown in FIG. 7. System 60 includes a number of the same components as system 2 shown in FIG. 1 and system 2' shown in FIG. 4, and like components are labeled with like reference numerals. System 60, however, includes a patient interface device 62 having a headgear component 64 according to a further alternative exemplary embodiment of the present invention.

Figure 8:
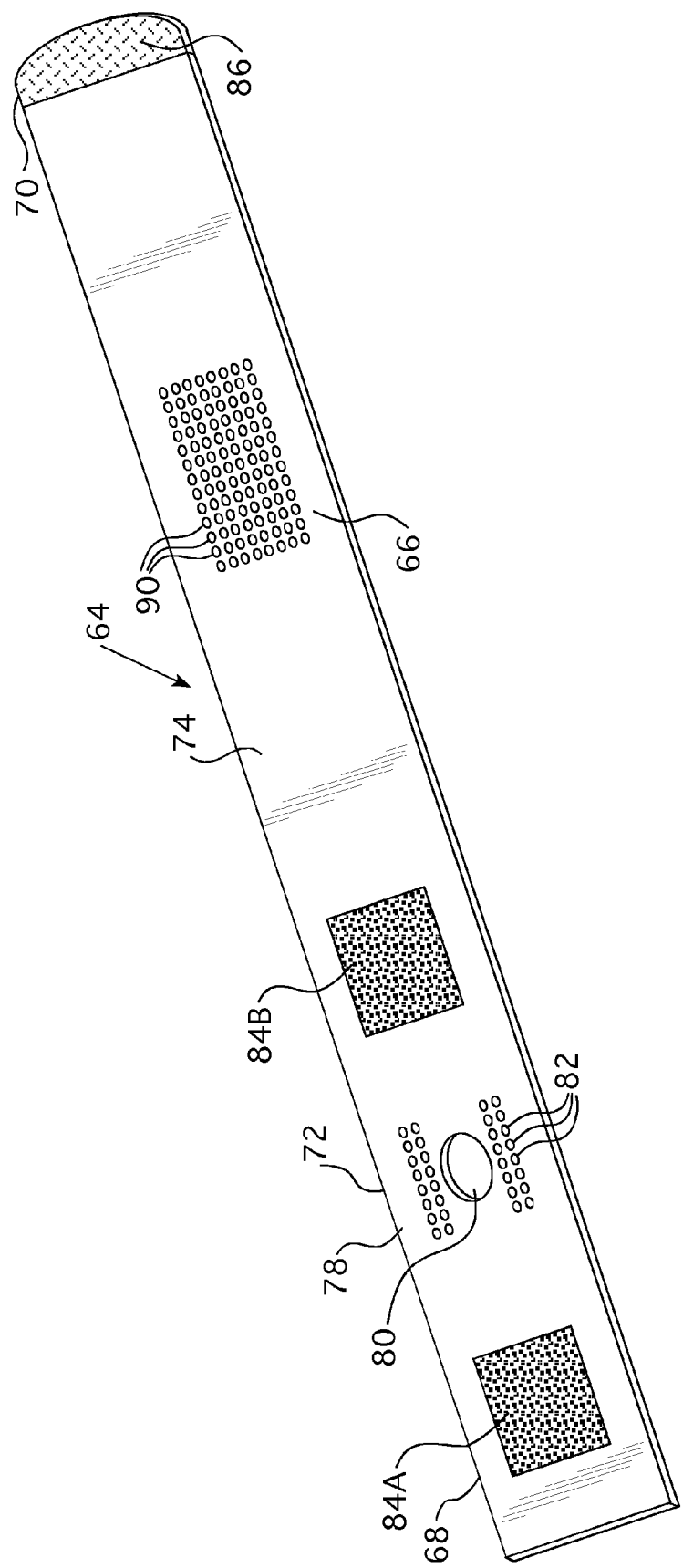
FIG. 8 is a rear perspective view and FIG. 9 is a front perspective view of a headgear component according to another exemplary embodiment of the present invention forming a part of the system of FIG. 7.
Figure 9:
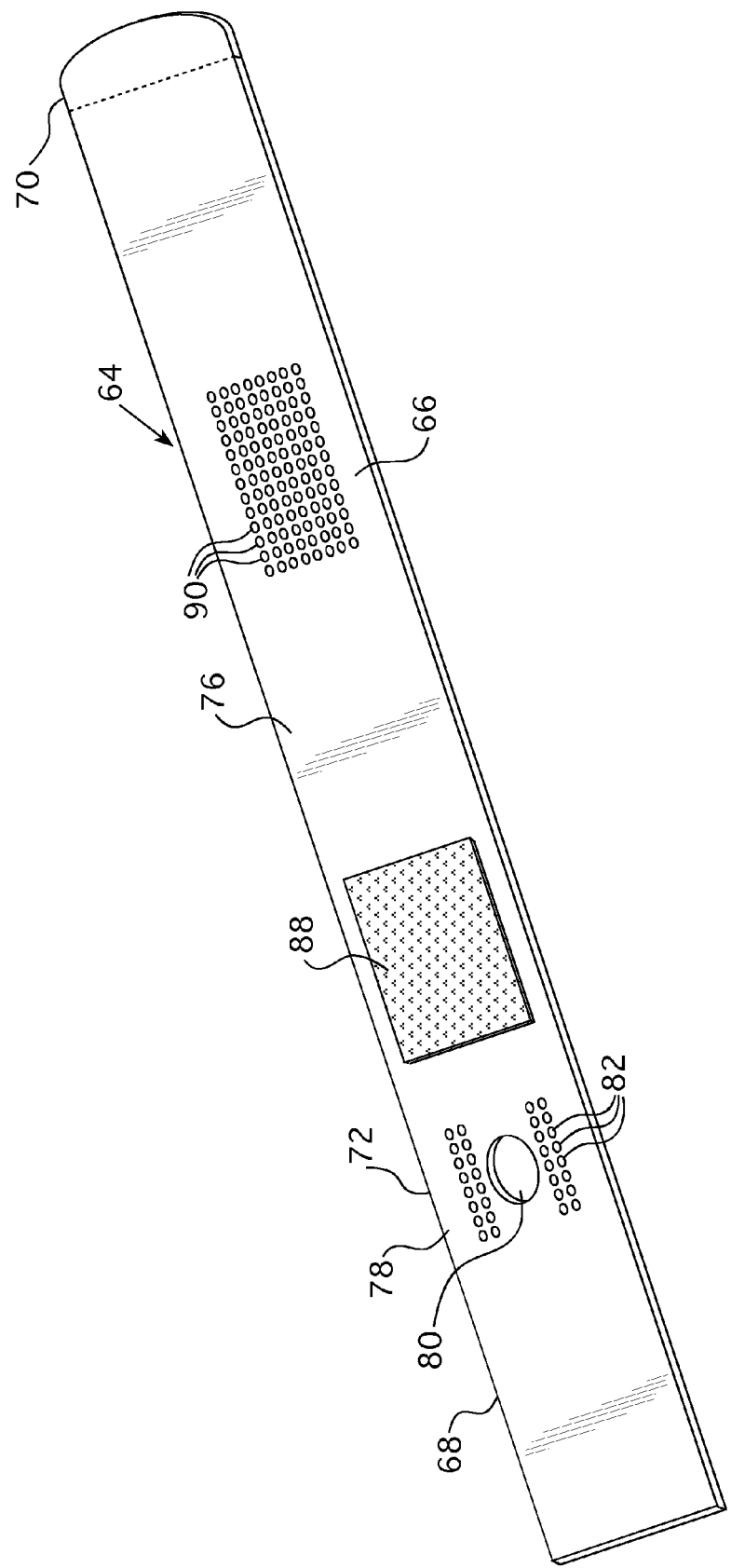

FIG. 8 is a rear elevational view and FIG. 9 is a front elevational view of headgear component 64. Headgear component 64 includes a flat, elongated body member 66 made of a fabric material. Body member 66 may be made from any of a number of suitable fabric materials, such as, without limitation, Lycra® (or another type of spandex material), silk, or polyester. Body member 66 includes a first end 68, a second end 70 opposite first end 68, a facial region 72 located adjacent to first end 68, a rear surface 74 (FIG. 8) and a front surface 76 (FIG. 9).

Facial region 72 includes a sealing interface region 78 having a main hole 80 and a plurality of vent holes 82 provided on either side of main hole 80. Main hole 80 and each of the vent holes 82 extend through main body member 66. As seen in FIG. 7, and as described elsewhere herein, main hole 80 is structured to receive fluid coupling conduit 10 therethough when patient interface device 62 is donned by the patient. Facial region 72 also includes first and second stabilizing regions 84A, 84B provided on rear surface 74 adjacent to and on opposite sides of sealing interface region 76. In the exemplary embodiment, first and second stabilizing regions 84A, 84B are similar to stabilizing regions 36A, 36B described elsewhere herein, and thus each comprises an elastomeric webbing made by coating the fibers of the fabric material of body member 66 in that region with an elastomer coating. Alternatively, first and second stabilizing regions 84A, 84B can be separate components attached to rear surface 74 as also described elsewhere herein. The first and second stabilizing regions 84A, 84B thus provide a stabilizing, slide prevention area on either side of sealing interface region 78 such that torque due to, for example, pulling on a hose forming part of patient circuit 6 during use is absorbed within the elastomeric webbing and fleshy regions of the patient's face that are in contact with the elastomeric webbing.

In addition, in the exemplary embodiment, as seen in FIG. 8, first end 70 on rear surface 74 includes a hook portion 86 of a hook and loop fastener system (such as a Velcro® system). As seen in FIG. 9, a loop portion 88 of the hook and loop fastener system is provided on front surface 76 in facial region 72 adjacent to sealing interface region 78. In addition, a plurality of vent holes 90 extending through body member 66 are provided adjacent to hook portion 86.

When patient interface device 62 is to be used by a patient, the patient first attaches fluid coupling conduit 10 to frame 14 as described elsewhere herein and then inserts fluid coupling conduit 10 through main hole 80 from rear surface 74 to front surface 76. When this is done, at least part of cushion 12 will be covered by the part of sealing interface region 78 surrounding main hole 80. The patient then positions cushion 12 against his or her nose as directed, places first end 68 against his or her left cheek, wraps body member 66 around his or her head as shown in FIG. 7, and engages hook portion 86 with a portion of loop portion 88 when the appropriate fit/tension is established. When this is done, the part of body member 66 that includes vent holes 90 will cover sealing interface region 78, cushion 12 and at least part of fluid coupling conduit 10 as seen in FIG. 7. Also, as seen in FIG. 7, portions of body member 66 will rest across the patient's ears, providing warmth and muffling sounds that could awaken the sleeping patient. It will be appreciated that patient interface device 62 may also be donned by positioning first end 68 against the patient's right cheek and wrapping body member 66 around the patient's head in the opposite direction.

In an alternative embodiment, rather than being flat, body member 66 may have a tubular constriction similar to body member 40 shown in FIGS. 4-6. In such an embodiment, two holes similar to holes 54, 56 would be provided in body member 66 to receive and hold cushion 12 as described elsewhere herein.

Thus, designs described herein in the various embodiments provide comfortable and easy to use patient interface devices that should positively affect a patient's adherence and compliance to therapy.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
   a headgear component including an elongated fabric body member adapted to wrap around a head of a patient, the elongated fabric body member having a first end, a second end and a sealing interface region located between the first end and the second end, the sealing interface region having a hole extending through the elongated fabric body member;
   a mask component having a cushion; and
   a fluid coupling conduit fluidly coupled to the cushion, wherein at least a portion of the fluid coupling conduit extends through the hole and the sealing interface region covers at least a portion of the cushion, and wherein the cushion is adapted to be held and supported by the elongated fabric body member in engagement with a portion of the patient's face responsive to the patient interface device being donned by the patient by wrapping the elongated fabric body member around the head of the patient, wherein the elongated fabric body member includes a rear surface and a front surface, the headgear component further comprising a first stabilizing region provided on the rear surface adjacent to a first side of the sealing interface region, and a second stabilizing region provided on the rear surface adjacent to a second side of the sealing interface region opposite the first side, wherein the first and second stabilizing regions each have a structure adapted to engage the patient's face and prevent the elongated fabric body member from sliding relative to the patient's face when the patient interface device is donned by the patient.

2. The patient interface device according to claim 1, wherein the first and second stabilizing regions each comprise an elastomeric webbing.

3. The patient interface device according to claim 2, wherein each elastomeric webbing comprises a plurality of fibers of the elongated fabric body member coated with an elastomer coating.

4. The patient interface device according to claim 2, wherein the first stabilizing region comprises a first separate component attached to the elongated fabric body member, wherein the first separate component comprises a first fabric piece wherein a plurality of fibers of the first fabric piece are coated with an elastomer coating, and wherein the second stabilizing region comprises a second separate component attached to the elongated fabric body member, wherein the second separate component comprises a second fabric piece wherein a plurality of fibers of the second fabric piece are coated with an elastomer coating.

5. The patient interface device according to claim 1, wherein the first end includes a first elastomeric webbing portion and the second end includes a second elastomeric webbing portion.

6. The patient interface device according to claim 5, wherein each elastomeric webbing portion comprises a plurality of fibers of the elongated fabric body member coated with an elastomer coating.

7. The patient interface device according to claim 5, wherein the elongated fabric body member includes a rear surface and a front surface, wherein the first elastomeric webbing portion comprises a first rear webbing portion provided on the rear surface and a first front webbing portion provided on the front surface, and wherein the second elastomeric webbing portion comprises a second rear webbing portion provided on the rear surface and a second front webbing portion provided on the front surface.

8. The patient interface device according to claim 1, wherein the elongated fabric body member comprises a flat body member.

9. The patient interface device according to claim 1, wherein the elongated fabric body member comprises a tubular body member.

10. A patient interface device, comprising:
a headgear component including an elongated fabric body member adapted to wrap around a head of a patient, the elongated fabric body member having a first end, a second end and a sealing interface region located between the first end and the second end, the sealing interface region having a hole extending through the elongated fabric body member;
a mask component having a cushion; and
a fluid coupling conduit fluidly coupled to the cushion, wherein at least a portion of the fluid coupling conduit extends through the hole and the sealing interface region covers at least a portion of the cushion, and wherein the cushion is adapted to be held and supported by the elongated fabric body member in engagement with a portion of the patient's face responsive to the patient interface device being donned by the patient by wrapping the elongated fabric body member around the head of the patient, wherein the elongated fabric body member comprises a tubular body member, wherein the tubular body member includes a rear surface and a front surface, wherein the hole is provided in the front surface, wherein a second hole is provided in the rear surface in the sealing interface region, wherein at least a portion of the mask component is held in between the rear surface and the front surface, and wherein at least a portion of the cushion extends outwardly through the second hole.

11. The patient interface device according to claim 1, wherein the sealing interface region is located midway between the first end and the second end.

12. A patient interface device, comprising:
a headgear component including an elongated fabric body member adapted to wrap around a head of a patient, the elongated fabric body member having a first end, a second end and a sealing interface region located between the first end and the second end, the sealing interface region having a hold extending through the elongated fabric body member;
a mask component having a cushion; and
a fluid coupling conduit fluidly coupled to the cushion, wherein at least a portion of the fluid coupling conduit extends through the hole and the sealing interface region covers at least a portion of the cushion, and wherein the cushion is adapted to be held and supported by the elongated fabric body member in engagement with a portion of the patient's face responsive to the patient interface device being donned by the patient by wrapping the elongated fabric body member around the head of the patient, wherein the elongated fabric body member includes a rear surface and a front surface, wherein the sealing interface region is located adjacent to the first end, wherein the second end includes a first fastening system component provided on the rear surface, wherein a second fastening system component is provided on the front surface adjacent to the sealing interface region, and wherein the second end is structured to cover the sealing interface region and the first fastening system component is structured to engage the second fastening system component when the elongated fabric body member is wrapped around the head of the patient, further comprising a plurality of vent holes in the second end and in the sealing interface portion.

13. The patient interface device according to claim 12, wherein the first and second fastening system components are part of a hook and loop fastener system.

14. A method of securing a patient interface device to a head of a patient, the patient interface device including a mask component having a cushion and a fluid coupling conduit fluidly coupled to the cushion, the method comprising:
obtaining a headgear component including an elongated fabric body member adapted to wrap around the head of the patient, the elongated fabric body member having a first end, a second end and a sealing interface region located between the first end and the second end, the sealing interface region having a hole extending through the elongated fabric body member, wherein the elongated fabric body member includes a rear surface and a front surface, the headgear component further comprising a first stabilizing region provided on the rear surface adjacent to a first side of the sealing interface region, and a second stabilizing region provided on the rear surface adjacent to a second side of the sealing interface region opposite the first side, wherein the first and second stabilizing regions each comprise an elastomeric webbing;
inserting a portion of the fluid coupling conduit through the hole such that the sealing interface region covers at least a portion of the cushion;
positioning the cushion against a portion of the patient's face; and
wrapping the elongated fabric body member around the head in a manner wherein the cushion is adapted to be held and supported by the elongated fabric body member in engagement with the portion of the patient's face.

15. The method according to claim 14, further comprising securing the first end and the second end together.

16. The method according to claim 15, wherein the securing the first end and the second end together comprises tying a knot between the first end and the second end.

17. The method according to claim 15, wherein the first end includes a first elastomeric webbing portion and the second end includes a second elastomeric webbing portion, and wherein the securing the first end and the second end together comprises twisting the first end and the second end together to cause the first and second elastomeric webbing portions to adhere to one another.

18. The method according to claim 14, wherein the sealing interface region is located adjacent to the first end, wherein the second end includes a first fastening system component provided on the rear surface, wherein a second fastening system component is provided on the front surface adjacent to the sealing interface region, and wherein the wrapping comprises positioning the first end on a cheek of the patient and wrapping the elongated fabric body member around the head such that the second end covers the sealing interface region and the first fastening system component is positioned to engage the second fastening system component.

* * * * *